United States Patent [19]

Aoki et al.

[11] Patent Number: 4,749,274
[45] Date of Patent: Jun. 7, 1988

[54] APPARATUS FOR DETECTING FUEL MIXTURE RATIO

[75] Inventors: Keiji Aoki; Shinji Ikeda, both of Susono, Japan

[73] Assignee: Toyota Jidosha Kabushiki Kaisha, Toyota, Japan

[21] Appl. No.: 6,064

[22] Filed: Jan. 22, 1987

[30] Foreign Application Priority Data

Jan. 24, 1986 [JP] Japan .................. 61-9383[U]
Feb. 1, 1986 [JP] Japan .................. 61-13383[U]

[51] Int. Cl.⁴ .................................. G01N 21/43
[52] U.S. Cl. .................................... 356/136
[58] Field of Search ............. 356/128, 133, 135, 136, 356/137

[56] References Cited

U.S. PATENT DOCUMENTS 4,438,749 3/1984 Schwippert ............... 356/133
4,641,965 2/1987 Harmer ..................... 356/135

FOREIGN PATENT DOCUMENTS

2642891 3/1978 Fed. Rep. of Germany ...... 356/135
2578978 9/1986 France ....................... 356/136
56-98540 8/1981 Japan .
129235 8/1983 Japan ......................... 356/128
2008793 6/1979 United Kingdom ............. 356/135
2085611 4/1982 United Kingdom ............. 356/128

Primary Examiner—F. L. Evans
Attorney, Agent, or Firm—Cushman, Darby & Cushman

[57] ABSTRACT

A prism has at least two optical planes and one of the planes is a boundary plane with mixed fuel. On one of two planes, a light emitting element is mounted and illuminates light to the boundary plane through the prism. A light receiving element receives light reflected from the boundary plane and converts the reflected light into electrical signals. Then a detector modifies the electrical signals from the light emitting element according to the detecting result and outputs them as detecting signals representative of the fuel mixture ratio. The temperature of the mixed fuel may be detected by a temperature sensor in which case the electrical signals are also modified to compensate for temperature changes of the mixed fuel.

5 Claims, 7 Drawing Sheets

APPARATUS FOR DETECTING FUEL MIXTURE RATIO

BACKGROUND ART

1. Field of the Invention

The present invention relates to apparatus for detecting a fuel mixture ratio and in particular to an apparatus which detects the fuel mixture ratio of mixed fuel containing two different kinds of fuel, for example like gasoline and alcohol. More precisely it relates to apparatus for detecting a fuel mixture ratio which detects optically, by utilizing a change of an absolute refractive index in accordance with the fuel mixture ratio.

2. Prior Art

Two kinds of apparatus for detecting a fuel mixture ratio have been proposed and developed. One kind detects the mixture ratio from a dielectric constant of mixed fuel as mentioned in Published Unexamined Japanese patent application No. Sho 56-98540, and another kind detects the mixture ratio from the absolute refractive index of mixed fuel as mentioned in U.S. Pat. No. 4,438,749.

Thus, the former of the above-mentioned detection apparatus detects the fuel mixture ratio utilizing the fact that the dielectric constant of the mixed fuel changes in proportion to the fuel mixture ratio, according to the difference of the dielectric constant of the fuel to be mixed, while the latter detection apparatus detects the fuel mixture ratio optically, utilizing the fact that the absolute refractive index of the mixed fuel changes in proportion to the fuel mixture ratio, according to the difference of the absolute refractive index of the fuel to be mixed. In the case of detecting the dielectric constant of fuel like the former apparatus, there is a problem that the detecting result varies widely, according to the temperature or the flow of fuel, or to impurities. Therefore, the other kind which detects the change in the absolute refractive index of the fuel optically, like the latter one above-mentioned, is favored.

In the prior apparatus for detecting the fuel mixture ratio by using the change in the absolute refractive index of the above-mentioned mixed fuel, a glass stick with a light emitting element and a light receiving element on opposite ends is mounted in the mixed fuel, the light emitting element emits light toward the side of the glass stick (the boundary surface with fuel) and the light receiving element receives light that is reflected from the boundary surface, as mentioned in U.S. Pat. No. 4,438,749.

Since a critical angle wherein illuminated light from the light emitting element all reflects varies in accordance with a change of a reflective index of mixed-fuel and reflected light to be received at the light receiving element varies according to fuel mixture ratio, this apparatus aims to detect the change by a detecting signal from the light receiving element and to detect the fuel mixture ratio. However, in this case, the light emitting element is attached to one end of the long glass stick, and therefore, there exists a problem that it is difficult to determine an illuminating angle correctly and that detecting signals of each detection apparatus scatter. This means that if an illuminating angle from a light emitting element scatters, the quantity of light reflected from the boundary surface between the side of a glass stick and fuel changes and an output signal from a light receiving element, in other words a detecting signal of fuel mixture ratio scatters.

In the above-mentioned detection apparatus, the light emitting element and a light receiving element are attached to opposite ends of the glass stick, face to face and the light receiving element receives direct light from the light emitting element with reflected light from the boundary surface which varies according to fuel mixture ratio. Therefore, there is a problem that the change of reflected light that indicates fuel mixture ratio cannot be captured sufficiently as detecting signals and that it is weak because of included noise signals.

SUMMARY OF THE INVENTION

The object of the present invention is to provide an apparatus for detecting a fuel mixture ratio in which stable detecting signals can be had at all times without an illuminating angle from a light emitting element scattering and in which the detecting signals vary sufficiently according to the change of the absolute refractive index of the fuel and anti-noise is improved.

To solve the above-mentioned problems, the present invention optically detects the fuel mixture ratio of mixed fuel containing two different kinds of fuel optically. The apparatus features a triangular prism having three optical planes of which one is a boundary plane with the above-mentioned mixed fuel and a light emitting element attached to the other two planes of the triangular prism illuminates the above-mentioned boundary plane through the prism. The apparatus also has a light receiving element which receives light reflected from the boundary plane and which convert the reflected light into electrical signals. A detector controls the illuminated light from the light emitting element at a fixed magnitude and detects and outputs electrical signals which can be had at the light receiving element. The light emitting element and the light receiving element are mounted so that the light emitting element illuminates the plane at or near the critical angle where the fuel of which the absolute refractive index differs sufficiently from the absolute refractive index of the triangular prism is to be the target fuel for detection between the two different fuels and the light receiving element receives the reflected light.

In such apparatus for detecting the fuel mixture ratio of two different fuels constituting the mixed fuel, in case the proportion of the fuel of which the absolute refractive index differs sufficiently from the absolute refractive index of the triangular prism is large, the quantity of light received by the light receiving element is large. Conversely, as the proportion of fuel of which the absolute refractive index is close to the absolute refractive index of the triangular prism gets larger, the quantity of light received by the light receiving element gets smaller. Therefore, the electrical signals received at the light receiving element (in other words, detecting signals from the detector) vary according to the fuel mixture ratio. This is because the light illuminating the boundary plane at an angle below the critical angle determined by the relative refractive index of the triangular prism and by the mixed fuel penetrates the fuel in accordance with the incident angle, thereby reducing the reflected light transmitted to the light receiving element.

In addition, in the present invention, the triangular prism is used to pass light from the light emitting element to the light receiving element, which are attached to each of the planes, so that the illuminating angle from the light emitting element to the boundary plane can be definite.

According to other features of the present invention, the fuel mixture ratio detection apparatus provides a prism of which one of the planes is to be the boundary plane with the mixed fuel. Light emitting means are attached to the other plane of the prism for illuminating parallel light to the boundary plane at a fixed angle through the prism. Light receiving means faces the boundary plane of the prism for receiving light which penetrates the boundary plane and the mixed fuel and for converting it to electrical signals. Additionally provided are a temperature sensor for detecting a temperature of the mixed fuel, and a detector for modifying an electrical signal from the light-receiving means according to the detecting result of the temperature sensor and for outputting it as a detecting signal representative of fuel mixture ratio.

The light emitting means is to illuminate parallel light to the other plane (boundary plane) of a prism opposite to the plane touched by mixed fuel. Light emitting elements such as light emitting diode, electro luminescence (EL), semi-conductor laser (LD) and rod lens for adjusting light from the light emitting element to parallel light are employed.

The light receiving means facing the boundary plane of the prism is to receive light transmitted from the boundary plane and to detect the magnitude of the transmitted light. Photoconduction elements such as a photodiode or phototransistor can be used for this purpose. Since this light receiving means receives light transmitted from the boundary plane of the prism through mixed fuel, it should be sealed with something like glass so that fuel may not be contained in the detecting elements.

In addition, it is desirable that the angle of incidence to the boundary plane of parallel light illuminated from the above-mentioned light emitting means should be close to a critical angle where absolute refractive index of detecting fuel to be detected differs sufficiently from the prism.

As the absolute refractive index of the fuel gets closer to that of the prism, the critical angle gets greater and light becomes easier to transmit. On the other hand, as the absolute refractive index of fuel differs more and more from that of the prism, the critical angle gets smaller and light gets more difficult to transmit. Therefore, if light is illuminated at this critical angle, a light receiving element receives light with this fuel being 100%, and as the proportion of this fuel gets smaller, the quantity of light received at the light receiving element gets greater to whereby increasing the variation for the change of detected signals corresponding to that of the mixture ratio.

Another means to enlarge the variation due to the change of the mixture ratio of detecting signals is enlargement of the critical angle of fuel whose absolute refractive index is even closes to that of prism.

Therefore, it is desirable to compose the prism with the material of which refractive index is very close to the fuel refractive index. For example, in the case of apparatus for detecting the fuel mixture ratio of mixed fuel of gasoline having a refractive index 1.434 and methanol having a refractive index 1.328, it is desirable to use fused quartz with a refractive index 1.456 which is closer to the refractive index of gasoline. In this case, an angle of incidence from the above-mentioned light emitting means to the boundary plane is to be near a critical angle of 65.8° ($=\sin^{-1} 1.328/1.456$) at the time when methanol is 100%.

In the present invention a temperature sensor may be used for detecting a temperature of fuel and electrical signals transferred photoelectrically are modified by the detecting signals from this temperature sensor so that the change of detecting signals caused by the change of the refractive index of fuel or prism, or by the change of the characteristics of light receiving elements or light emitting elements according to the change of the temperature of fuel may be compensated.

In the present apparatus for detecting fuel mixture ratio constituted in this way, parallel light illuminated from the light emitting means is penetrated from the boundary plane of the prism to the fuel side, according to the change of the refractive index of the mixed fuel and the quantity of penetrated light is detected at the light receiving means.

This detecting result is modified according to the fuel temperature and the fuel refractive index or the fuel mixture ratio is to be detected precisely without being related to the change of the temperature.

These and other objects and advantages of the invention will become apparent upon reference to the following, specification, attendant claims, and drawings.

DETAILED DESCRIPTION OF THE PREFERRED EMBODIMENTS

Figure 1:
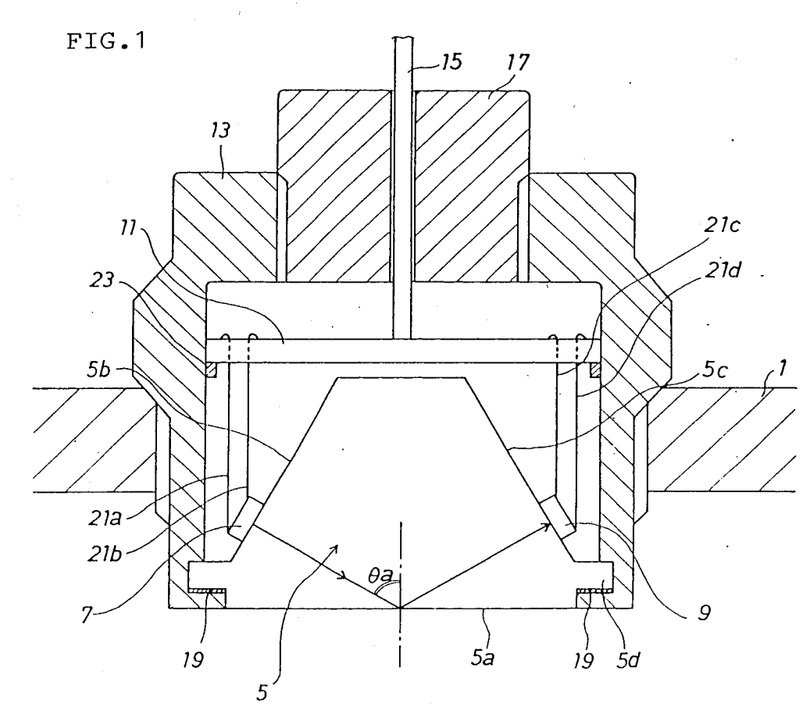
FIG. 1 is a cross-section illustrative of the whole construction of apparatus according to this invention for detecting a fuel mixture ratio.

FIG. 1 shows a cross-sectional view illustrative of an apparatus for detecting a fuel mixture ratio of mixed methanol and gasoline according to the present invention. The detecting apparatus is mounted in a fuel tank 1 and has three photoelectric planes 5a, 5b and 5c forming the sides of a generally triangular prism 5 truncated at its top. Plane 5a is considered to be a boundary plane relative to mixed fuel in the fuel tank 1. A light emitting element 7 is attached to one of the other two planes 5b, 5c of the triangular prism 5, a light receiving element 9 is attached to the other for receiving light reflected from the boundary plane 5. A detector base 11 is equipped with a detector which transmits light to the boundary plane 5a and actuates the light emitting element 7 and outputs electrical signals received at the light receiving element 9 as detecting signals representative of the fuel mixture ratio. Distributor body 13 holds and protects prism 5 and the detector base 11 and fixes the detecting apparatus to the fuel tank. A signal conductor 15 provides the detector of the detector base 11 with power-supply voltage and takes out the output signals from the detector. A cover protector 17 protects this signal line 15 and the detector base 11 and so on in the distributor body 13.

Prism 5 is mounted to the distributor body 13 by mounting protrusion 5d formed around the boundary plane 5a of the triangular prism 5 at the tip of the distributor body 9, and a seal member 19 is provided at this mounted part so that fuel may not escape in the distributor body 13. Light emitting and receiving elements 7 and 9 are connected to the detector base 11 through lead lines 21a through 21d, and detector base 11 is mounted in the distributor body 13 through an engaging member 23.

Figure 2:
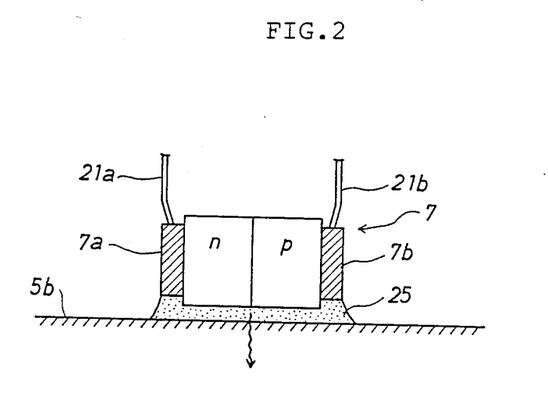
FIG. 2 is a cross-section illustrating the mounting of a light emitting element at the triangular prism.

FIG. 2 shows the light emitting element 7 being composed of a light emitting diode including a connected semiconductor of P type and N type consisting of gallium arsenic (GaAs). In this light emitting element 7, infrared light is generated from the connected plane of each semi-conductor by applying power-supply voltage from the detector base 11 to electric poles 7a and 7b formed on the P type and N type semi-conductor respectively through lead lines 21a and 21b, and infrared light is transmitted to the triangular prism 5 through ceramic adhesive 25.

Figure 3:
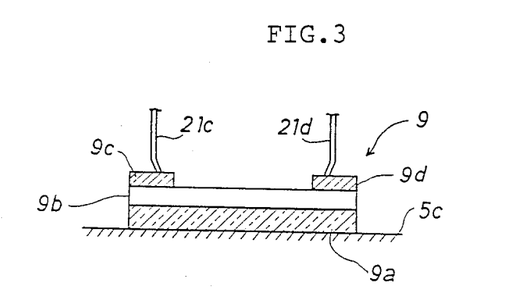
FIG. 3 is a cross-sectional view illustrating of the mounting of a light receiving element at the triangular prism.

In FIG. 3, the light receiving element 9 is shown composed of a transparent glass substrate 9a attached to the plane 5c of the prism 5, a photoconduction element 9b made of cadmium sulfide formed on the glass substrate 9a as a thin film, and electric poles 9c and 9d mounted at opposite end of the photoconduction element 9b. In this light receiving element 9, if reflected infrared light transmitted from the light emitting element 7 to the boundary plane 5a of prism 5 enters the photoconduction element 9b through the glass substrate 9a, the value of resistance of the photoconduction element 9b varies in response to the magnitude of the reflected light.

In addition, when the fuel is 100% methanol, the light emitting element 7 and the light receiving element 9 are relatively disposed so that the light receiving element 9 receives the reflected light at a critical angle relative to the boundary plane 5a.

Therefore, assuming that prism 5 is formed with fused quartz which has a refractive index of 1.456, the refractive index of methanol being 1.328, the critical angle theta ($\theta$) where incident light reflects would be about 65.8° by the following formula.

$$\theta = \sin^{-1}\frac{1.328}{1.456}$$

As shown in FIG. 1, $\theta$ a is set at 65.8° or a little below.

This is because the refractive index of gasoline of 1.434 is closer to that of fused quartz and, reduces the proportion of methanol, so that the critical angle becomes larger, incident light at the boundary plane 5a leaks out into the fuel side and as a result of that, reflected light becomes weak and the value of resistance of the light receiving element 9 becomes high. Therefore, methanol density can be detected from the change of the value of resistance of the light receiving element 9.

Figure 4:
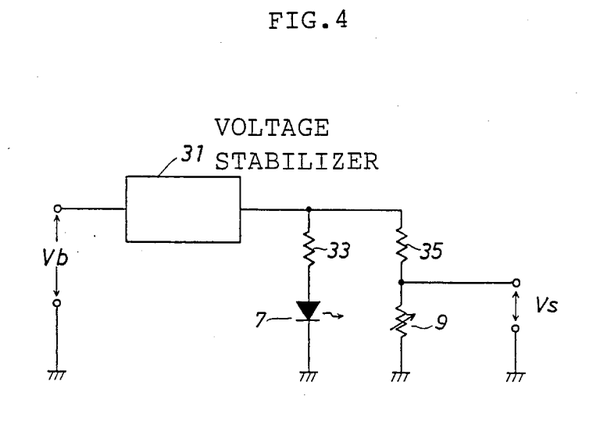
FIG. 4 is an electric circuit illustrating a light emitting element and a light receiving element connected according to the present invention.

FIG. 4 shows an electric circuit illustrative of the detector formed on the above-mentioned detector base 11, the light emitting element 7 and light receiving element 9.

As can be seen in the FIG. 4, the detector includes a voltage stabilizer 31 which controls the power-supply voltage Vb at a constant voltage, a resistance 33 for current control which divides that the constant voltage relative to element 7 and controls the electric current flowing through the light emitting element 7. The detector also includes a resistance 35 for voltage conversion which divides the constant voltage relative to element 9 and applies the divided voltage to the light receiving element 9 in order to detect the value of resistance of the light receiving element 9 as voltage signals to provide an output voltage Vs generated across light receiving element 9 as detecting signals.

As the foregoing description shows, if power-supply voltage is applied to the detector, the light emitting element 7 is actuated and the infrared light is transmitted to the boundary plane 5a. Then at the boundary plane 5a, the infrared light passes through and reflects from that plane according to fuel mixture ratio and the light receiving element 9 receives the reflected light. As the value of resistance of the light receiving element 9 varies in accordance with the magnitude of the reflected light, detecting signals corresponding to the fuel mixture ratio are output from the detector, and the fuel mixture ratio or methanol density can be determined by these detecting signals.

Figure 5:
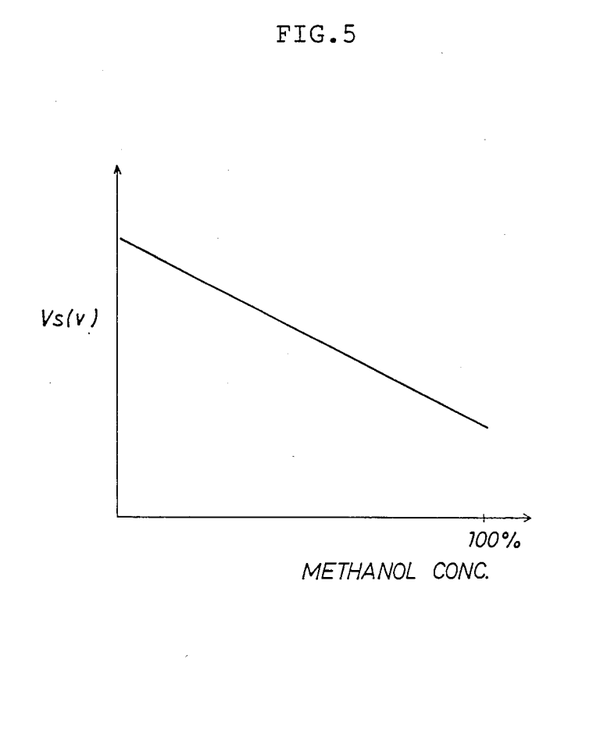
FIG. 5 is a graph of signals for the detector versus methanol concentration.

As shown by FIG. 5, the relation between these detecting signals and methanol density is that the larger the proportion of methanol becomes, the smaller the detecting signal Vs becomes. This means that if the proportion of methanol is large, infrared light is reflected easily to the boundary plane 5a, and on the contrary, if the proportion of gasoline is large, infrared light penetrates the boundary plane 5a and it is difficult for infrared light to be reflected to the side of the light receiving element 9.

Here, the present invention is constructed as the light emitting element 7 or the light receiving element 9 being formed directly on the triangular prism 5, so that emitted light from the light emitting element 7 should be transmitted into the triangular prism 5 without a loss and the light receiving element 9 should catch reflected light from the boundary plane 5a without a loss. However, in general, a light emitting element or a light receiving element marketed as a unit may be attached. As a light emitting element 7, everything that emits light can be used, and an electroluminescence (EL) element or semi-conductor laser other than light emitting diode can be used.

In addition, as a light catching element 9, a phototransistor or photodiode besides a photoconduction element consisting of cadmium sulfide can be used as can anything which can receive light illuminated from a light emitting element 7 and from an available electrical signals representative of the magnitude of reflected light.

In the present embodiment, prism 5 has been explained that it is composed of fused quartz and it is to make detecting signals Vs change largely between 0% and 100% of methanol. However, anything that can withstand gasoline and alcohol and may be utilized as a prism can be used.

Thus, with the detecting apparatus of this embodiment, light emitted from the light emitting element 7 can be transmitted through a triangular prism without loss and the reflected light can be received by the light receiving element 9 without loss. Therefore, loss of electric power is small and the detecting level increased. Further, with the face of the light emitting element 7 and light receiving element 9 attached to the prism 5 so that the reflected light receiving angle is related to 100% methanol, the quantity of reflected light reaching the light receiving element is increased and the signal to noise ratio of detecting signals is improved. Besides the attachment position of the light emitting element 7 and the light receiving element 9 being easily adjusted on the planes 5b, 5c of the prism 5 and these elements being firmly mounted with adhesives and so on, the illuminating angle from the light emitting element 7 and the light receiving angle of the light receiving element 9 can be set precisely without scattering effect in any embodiment of this detecting apparatus.

The second embodiment of the present invention is now explained.

Figure 6:
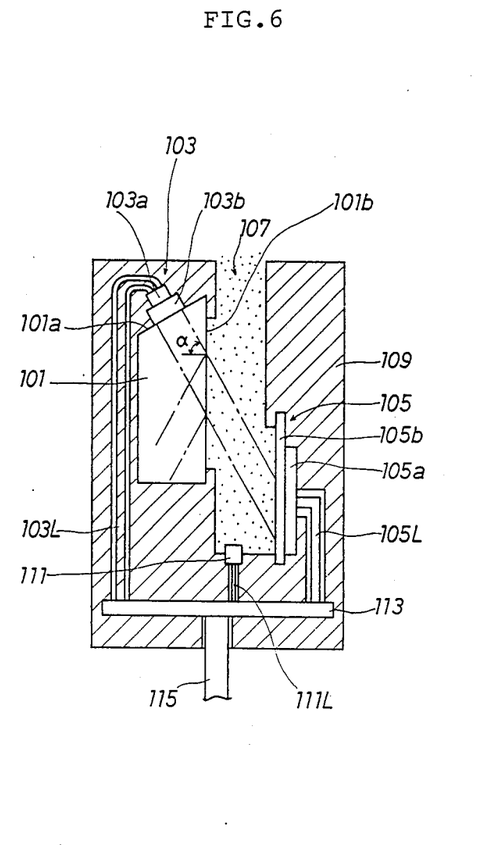
FIG. 6 is a cross-section illustrative of a second embodiment apparatus for detecting a fuel mixture ratio.

First, FIG. 6 shows a cross section of another fuel mixture ratio detecting apparatus of the present invention for detecting the fuel mixture ratio of a mixed fuel such as gasoline and methanol from the quantity of light penetrating through the boundary plane. Again, use is made of a quartz prism formed with fused quartz which is superior in chemical resistance and for which the refractive index is close to that of gasoline, one of the planes being the boundary plane with the mixed fuel.

As FIG. 6 shows, the apparatus for detecting fuel mixture ratio of the present embodiment is provided with a quartz prism 101, light emitting part 103 which transmits parallel light at a fixed angle alpha ($\alpha$) from one plane 101a of the quartz prism 101 to an other plane 101b which is the boundary plane relative to the mixed fuel in opening 107. A light receiving part 105 receives light penetrating the boundary plane 101b and the mixed fuel. A distributor body 109 mounts the quartz prism 101 and the light receiving part 105, face to face, through an opening 107 where mixed fuel enters.

As the present apparatus is used in the mixed fuel, distributor body 109 is composed of a resin which is superior in resistance to gasoline and alcohol, for example nitrile rubber, teflon rubber and so forth. Distributor body 109 contains light emitting part 103 mounted on the quartz prism 101, the lead lines 103L and 105L of the light emitting part 103 and light receiving part 105 and protects them from the mixed fuel except for the interior faces of prism 101 and light emitting part 105.

The light receiving part 105 is composed of the photoconductive cell 105a made of materials like CdS or CdSe of which the value of resistance varies according to the quantity of light received by fused quartz plane 105b which protects this photoconductive cell 105a from the mixed fuel at the interior plane which faces the quartz prism 101. The photoconductive cell 105a is also protected between the fused quartz plane 105b and the distributor body 109.

In addition, the light emitting part 103 is composed of the light emitting diode 103a and the rod lens 103b for converting emitted light from the light emitting diode into parallel light, and it is set to emit light at a fixed angle from one plane 101a of the quartz prism 101 to the boundary plane 101b. This illuminating angle is set at the critical angle 65.8° at which light is totally reflected from the boundary plane 101b when the mixed fuel is 100% methanol. Therefore, as the gasoline density of mixed fuel increases, quantity of penetrating light increases.

Disposed in the distributor body 109 is a thermistor 111 for detecting the temperature of the fuel along with lead line 111L for compensating for a change of the detecting characteristics of the detecting apparatus by a change of temperature of the mixed fuel.

A hybrid IC 113 having a detector is provided within the distributor body 109. The detector connects to lead lines 103L, 105L and 111L from the above-mentioned light emitting part 103, light receiving part 105, and thermistor 111 and actuates light emitting part 103 which emits parallel light inside the quartz prism 101. The detector then detects the quantity of light received at the photoconductive cell 105a and from the value of resistance thereof, modifies the detecting result by the value of resistance of the thermistor 111 and outputs detecting signals indicative of fuel mixture ratio. The signal conductor 115 applies power-supply voltage to this hybrid IC 113 and takes out the detecting signal.

Figure 7:
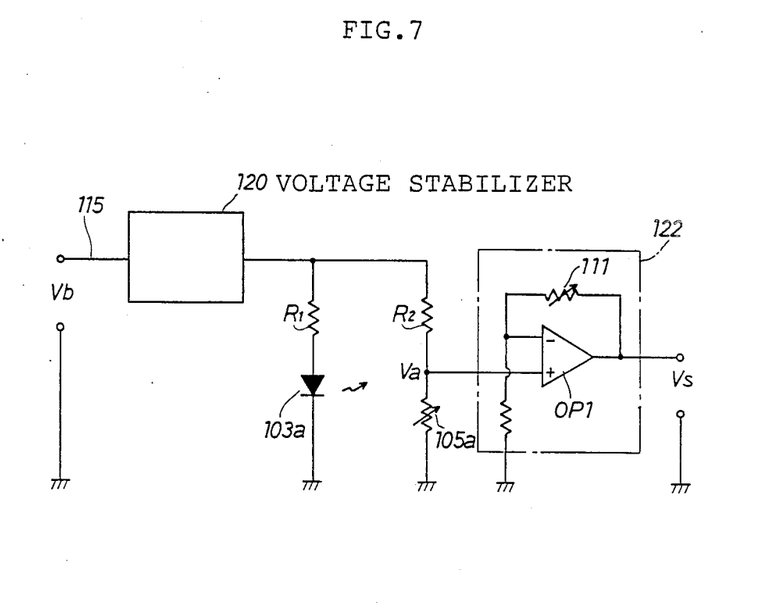
FIG. 7 is a diagram of an electric circuit for the second embodiment.

FIG. 7 shows an electric circuit illustrative of the detector of this hybrid IC 113.

As the figure shows, the detector includes the voltage stabilizer 120 which controls the power-supply voltage input through the signal conductor 115 at a constant voltage, the resistance R1 for current control which divides at constant voltage relative to diode 103 and controls electric current flowing through the light emitting diode 103a. Also, the resistance R2 for voltage conversion divides the constant voltage relative to photoconductive cell 105a to produce an output voltage Va. A non-inverting operational amplifier 122 including the operational amplifier OP1 amplifies the voltage Va across photoconductive cell 105a and outputs it as a detecting signal Vs indicative of the fuel mixture ratio. In addition, as the voltage generated across the photoconductive cell 105a increases in accordance with rise in fuel temperature. Thermistor 111 is used as one of the resistance which decides the amplification degree for the non-inverting operational amplifier 122, in order to compensate for the voltage change caused by the temperature change, so that detecting signals may not be influenced by the fuel temperature and may always be the value representative of the fuel mixture ratio.

Figure 8:
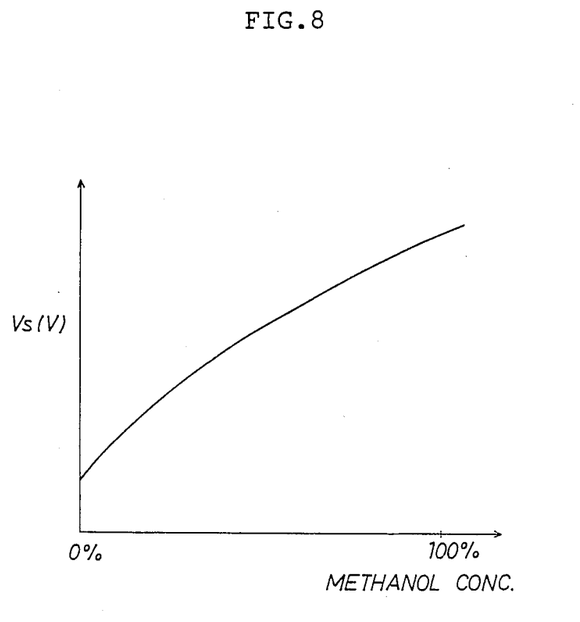
FIG. 8 is a graph illustrative of a relation between detecting signals and a methanol concentration in the second embodiment.

In the apparatus for detecting fuel mixture ratio of the present embodiment constructed above, if the power-supply voltage is applied to the detector, the light emitting diode 103a is actuated and parallel light is illuminated at the angle $\alpha$ to the boundary plane with the fuel of the quartz prism 101. Then the emitted light penetrates the boundary plane 101b according to the methanol density of the mixed fuel and the value of resistance of the photoconductive cell 105a varies according to the quantity of penetrating light. Therefore, the detecting signal Vs which has the characteristics shown in the FIG. 8 is output from the detector in response to the methanol density from the change of the value of resistance of the photoconductive cell 105a and the methanol density can be determined from this detecting signal Vs. The voltage generated at across photoconductive cell 105a changes according to the change of the refractive index of the quartz prism 101 or the mixed fuel caused by the change of the fuel temperature, or the characteristic change of the light emitting diode 103a or the photoconductive cell 105a. This change is compensated by the thermistor mounted on the non-inverting operational amplifier, so that the detecting signals corresponding to the fuel mixture ratio are always available.

In the present embodiment, the prism includes the fused quartz which has a refractive index close to that of gasoline and the angle of incidence of the parallel light transmitted to the boundary plane is set at the critical angle where the methanol is 100% to thereby enlarge or enhance the change of the quantity of penetrating light according to the change of the mixed fuel from methanol 100% to gasoline 100%, causing a corresponding change in the value of resistance of the photoconductive cell for the change of methanol density, and a change in the magnitude of the detecting signals. This means that the signal to noise ratio of the detecting signals is improved. In addition, in the present embodiment, since the detector is kept inside the distributor body 109 and the length of lead lines 103L, 105L, 111L respectively is shortened, the signal to noise ratio of the detecting signals is further improved.

Furthermore, in this embodiment, the illuminating angle from the light emitting part 103 to the boundary plane 101a is determined for sure only by mounting the light emitting part 103 along one of the planes of the quartz prism, so that it doesn't scatter with every detecting apparatus and stable detecting signals are available.

While a preferred embodiment of the invention has been described using specific terms, such description is for illustrative purpose only, and it is to be understood that changes and variations may be made without departing from the spirit or scope of the following claims.

What is claimed is:

1. Apparatus for optically detecting a fuel mixture ratio of mixed fuel that has two different kinds of fuel comprising:
   a prism, having three optical planes, one of said planes disposed to be a boundary plane with said mixed fuel;
   a sensor portion, comprising:
   (a) light emitting means mounted on another one of said planes for emitting light toward said boundary plane through said prism;
   (b) light receiving means, mounted on a third one of said planes, for receiving light reflected from said boundary plane through said prism and converting a magnitude of said reflected light into an electrical signal,
   said light emitting means and said light receiving means being relatively disposed so that said light emitting means illuminates light to said boundary plane at or near a predetermined angle at which one of said two kinds of fuel to be detected is more widely different in absolute refractive index from said prism than the other of said two kinds of fuel; and
   (c) detector means, connected to said light emitting means and to said light receiving means, for controlling said illuminating light from said light emitting means at a constant magnitude and for receiving said electrical signal and outputting a detected signal corresponding to said electrical signal;
   a distributor body, formed surrounding said two of said planes and coupled to said two of said planes of said prism at a contact zone to surround said light emitting means, said light receiving means, and said detector means; and
   sealing means, located at said contact zone, for sealing between said two of said optical planes and said distributor body, thereby enclosing said sensor portion.

2. Apparatus according to claim 1 wherein said detector means includes means for varying said detected signal in response to said fuel mixture ratio.

3. Apparatus according to claim 1 wherein said illuminating angle from said light emitting means to said boundary plane is controlled to be constant.

4. Apparatus according to claim 1 wherein said predetermined angle is a critical angle where said mixed fuel contains only one kind of fuels to be detected.

5. Apparatus as in claim 1 wherein said two of said planes of said prism are each formed with first engaging members thereon, and wherein said distributor body has two second engaging members thereon, said second engaging members being of a type adapted to engage with said first engaging members, and wherein said sealing means is provided between said first and second engaging means, for providing a seal therebetween.

* * * * *